United States Patent
Martin

(10) Patent No.: US 9,084,836 B2
(45) Date of Patent: Jul. 21, 2015

(54) PREPARATION OF ELASTIC COMPOSITE STRUCTURES USEFUL FOR COMPONENTS OF DISPOSABLE HYGIENE PRODUCTS AND ARTICLES OF APPAREL

(75) Inventor: Kenneth Edward Martin, Newark, DE (US)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 1079 days.

(21) Appl. No.: 13/056,468

(22) PCT Filed: Aug. 5, 2009

(86) PCT No.: PCT/US2009/052854
§ 371 (c)(1),
(2), (4) Date: Jan. 28, 2011

(87) PCT Pub. No.: WO2010/017297
PCT Pub. Date: Feb. 11, 2010

(65) Prior Publication Data
US 2011/0174317 A1    Jul. 21, 2011

Related U.S. Application Data

(60) Provisional application No. 61/086,485, filed on Aug. 6, 2008.

(51) Int. Cl.
*A61F 13/00* (2006.01)
*A61L 15/26* (2006.01)

(52) U.S. Cl.
CPC ...................... *A61L 15/26* (2013.01)

(58) Field of Classification Search
USPC ................. 602/41–54; 128/888–889
See application file for complete search history.

(56) References Cited

U.S. PATENT DOCUMENTS

| | | | |
|---|---|---|---|
| 3,692,618 A | 9/1972 | Dorschner et al. | |
| 3,849,241 A | 11/1974 | Butin et al. | |
| 4,139,567 A | 2/1979 | Pruckmayer | |
| 4,340,563 A | 7/1982 | Appel et al. | |
| 4,482,666 A | 11/1984 | Reeves | |
| 4,634,482 A | 1/1987 | Lammers | |
| 4,720,415 A | 1/1988 | Vander Wielen et al. | |
| 6,491,776 B2 | 12/2002 | Alper et al. | |
| 6,639,041 B2 | 10/2003 | Nishikawa et al. | |
| 6,713,415 B2 | 3/2004 | Martin | |
| 2002/0119722 A1 | 8/2002 | Welch et al. | |
| 2003/0166821 A1 | 9/2003 | Pruckmayr et al. | |
| 2004/0006324 A1 | 1/2004 | Zhou et al. | |
| 2005/0142356 A1 | 6/2005 | Zhou | |
| 2006/0270821 A1 | 11/2006 | Palmer, Jr. et al. | |
| 2006/0276610 A1 | 12/2006 | Jenny et al. | |
| 2007/0117591 A1 | 5/2007 | Rached et al. | |
| 2007/0117953 A1 | 5/2007 | Palmer, Jr. | |
| 2008/0038512 A1 | 2/2008 | Burr et al. | |
| 2011/0174317 A1* | 7/2011 | Martin | 128/849 |

FOREIGN PATENT DOCUMENTS

| | | |
|---|---|---|
| EP | 1634557 | 3/2006 |
| WO | 80/00676 | 4/1980 |

* cited by examiner

*Primary Examiner* — Michael A. Brown
(74) *Attorney, Agent, or Firm* — Christina W. Geerlof

(57) ABSTRACT

Disclosed herein are articles and processes for making elastic composite structures which can be used as or converted into a component of disposable hygiene products or articles of apparel. At least one relatively inelastic substrate, for example a nonwoven substrate, is adhesively bonded with a hot melt adhesive to a certain selected type of elongated polyurethane material in the form of a film or one or more fibers or filaments. The elongated polyurethane material is then allowed to relax which provides an elastic composite structure which is gathered or puckered.

15 Claims, No Drawings

PREPARATION OF ELASTIC COMPOSITE STRUCTURES USEFUL FOR COMPONENTS OF DISPOSABLE HYGIENE PRODUCTS AND ARTICLES OF APPAREL

BACKGROUND OF THE INVENTION

1. Field of Invention

This invention relates to the preparation of elasticized composite structures which can be used as or converted into components of disposable hygiene products such as diapers. These composite structures are elasticized using polyurethane films or filaments to impart stretchability to the structures so prepared. A selected type of polyurethane or polyurethaneurea is extended to a relatively high draft and, in its stretched condition, is adhesively bonded to at least one relatively inelastic substrate with hot melt adhesive applied at relatively high temperature. The stretched polyurethane/substrate combination is then allowed to relax and retract to thereby provide an elasticized gathered or puckered stretchable composite which can provide stretchable components for use in disposable diapers or other disposable hygiene products or for use in articles of apparel.

2. Summary of the Related Technology

The use of elastomeric fibers, filaments and/or films in, for example, leg bands and other components of disposable diapers has been known for many years. In a typical process to produce these components, spandex fibers or filaments or natural or synthetic rubber film strips are elongated to a specific draft and adhesively attached to, for example, one or two layers of a nonwoven substrate using a hot melt adhesive. This provides good stretch and recovery properties to the diaper component, e.g., the nonwoven substrate, which has been elasticized by incorporation of the elastomeric fibers, filaments and/or film into or onto this component.

The adhesives used in this process are frequently those which must be heated to an elevated temperature in order to form a good bond between the elastomeric fiber, filament or film and the material of the diaper component being elasticized, for instance a nonwoven fabric or substrate. At this elevated temperature, the break tenacity of the elastomeric fiber, filament or film is significantly lower than its break tenacity at room temperature (~75° F.). If the break tenacity of the elastomeric fiber, filament or film at the elevated temperature experienced at the point of contact with the hot melt adhesive is lower than the first load force of the fiber, filament or film at room temperature and at the draft used in the elasticizing process, then the fiber, filament or film will break. It is thus commonly known that if the elastomeric fiber, filament or film is stretched to too great an extent or if the adhesive is heated to too high a temperature when it contacts the elastomer, excessive instances of breaks in the elastomeric fibers, filaments or film will occur during the process of preparing elasticized material for hygiene product components.

Typical process conditions for elasticizing material for diaper components with spandex and a hot melt adhesive involve use of a spandex fiber at a draft between 3.5 and 4.5 (250% to 350% elongation) and a standard elastic attachment hot melt adhesive temperature of about 260° F. to 325° F. (127° C. to 177° C.) when the adhesive is applied by a spiral spray process. If the spandex elongation is increased beyond 4.5 when the hot melt adhesive is applied, instances of breaks in the spandex at the point of adhesive application rapidly increase to an unacceptable level. If the adhesive temperature is decreased below about 260° F. (127° C.) to lessen the thermal load on the spandex fiber, the integrity of the bond between the spandex and the diaper component, e.g., nonwoven, decreases to an unacceptable level.

Breaks in the elastomeric fibers, filaments or film in the production of elasticized structures used for components of disposable hygiene products are highly undesirable. This is because when the elastomer breaks, the disposable product production line must be shut down; the elasticizing fibers, filaments or film must be re-strung; and the apparatus restarted. This causes significant down time, for example, of a diaper production line and generates a number of waste diapers.

Notwithstanding the availability of components for disposable hygiene products which have been elasticized by the adhesive attachment of spandex, it would be advantageous to identify selected combinations of materials (e.g., certain spandex materials and hot melt adhesives) and procedures for preparation of composite structures used for such components, which permit higher draft (elongation) of the spandex elasticizing material with minimized occurrence of spandex breaks upon contact of the spandex elasticizing agent with hot melt adhesives. Stretching spandex to greater elongation in turn would permit the use of less spandex to elasticize a given number of components, thereby minimizing costs. Alternatively, elongation of the high draft potential spandex only to an extent which is close to that used in conventional elasticizing procedures would permit the effective use of hot melt adhesives under conditions which induce fewer instances of breaks in the spandex, thereby also providing a reduced cost procedure.

SUMMARY OF THE INVENTION

One embodiment is directed to a articles including an elastic composite structure and processes for making an elastic composite structure which can be used as or converted into a component for incorporation into articles of apparel or disposable hygiene products such as disposable diapers.

An article including at least one relatively inelastic substrate, a polyurethane material selected form the group consisting of a film and one or more filaments including as the soft segment base of said polyurethane material a polyglycol comprising a poly(tetramethylene-co-alkylene ether)glycol comprising constituent units derived by copolymerizing tetrahydrofuran and a $C_2$ or $C_3$ alkylene oxide, wherein the portion of the units derived from $C_2$ or $C_3$ alkylene oxide comprises at least 15 mole % of said poly(tetramethylene-co-alkylene ether)glycol; and a hot melt adhesive having a temperature of from about 260° F. to about 350° F.

In another embodiment is a process for making an elastic composite structure, which process includes:

A) providing at least one relatively inelastic substrate;

B) providing a polyurethane material selected form the group consisting of a film and one or more filaments comprising as the soft segment base of said polyurethane material a polyglycol comprising a poly(tetramethylene-co-alkylene ether)glycol comprising constituent units derived by copolymerizing tetrahydrofuran and a $C_2$ or $C_3$ alkylene oxide, wherein the portion of the units derived from $C_2$ or $C_3$ alkylene oxide includes at least 15 mole % of said poly(tetramethylene-co-alkylene ether)glycol;

C) elongating in at least one direction said polyurethane material to a draft of from greater than about 4.5 to about 5.5;

D) applying to at least one surface of said at least one relatively inelastic substrate and/or to at least one surface of said elongated polyurethane material a hot melt adhesive having a temperature of from about 260° F. to about 350° F.;

E) contacting the adhesive-containing surfaces of said at least one relatively inelastic substrate and/or said polyurethane material with each other under conditions sufficient to adhesively bond said elongated polyurethane material to said at least one relatively inelastic substrate; and F) after adhesively bonding said elongated polyurethane material to said at least one relatively inelastic substrate, allowing said polyurethane material to relax, to thereby provide said elastic composite structure.

Also included is a process for making an elastic composite structure that is used as or is suitable for conversion into a component of disposable hygiene products or articles of apparel, which process includes:

A) providing at least one nonwoven substrate;

B) further providing a plurality of filaments of a polyurethane material comprising as the soft segment base of said spandex material a glycol copolymer of i) tetrahydrofuran; and ii) ethylene oxide, said ethylene oxide comprising at least 15 mole % of said glycol copolymer;

C) elongating in at least one direction said plurality of spandex filaments to a draft of from about 5.0 to about 5.4;

D) applying to at least one surface of said at least one nonwoven substrate and/or to the surfaces of said plurality of elongated spandex fibers a hot melt adhesive having a temperature of from about 300° F. to about 325° F.;

E) contacting the adhesive-containing surfaces of said at least one nonwoven substrate and said plurality of elongated filaments with each other under conditions sufficient to adhesively bond said plurality of elongated filaments to said at least one nonwoven substrate; and F) after adhesively bonding said plurality of elongated filaments to said at least one nonwoven substrate, allowing said plurality of elongated filaments to relax, to thereby provide said elastic composite structure.

In a further embodiment is a process for making an elastic multilayer composite laminate structure, which process includes:

A) providing at least two nonwoven substrates in the form of thermally bonded, spunbonded or hydroentangled webs of substantially equal width and having a basis weight of from about 10 to about 40 grams/m$^2$;

B) further providing a plurality of threadlines of a polyurethane or polyurethaneurea material including as the soft segment base of said spandex material a glycol copolymer of i) tetrahydrofuran; and ii) ethylene oxide, said ethylene oxide comprising from about 37 mole % to about 70 mole % of said glycol copolymer, each of said threadlines being at least 400 decitex;

C) interposing said plurality of threadlines between said at least two nonwoven substrates in a layer of substantially parallel, equally spaced, threadlines spaced such that there are at least eight threadlines per inch of nonwoven substrate width;

D) elongating to a substantially equal extent each of said threadlines to a draft of from greater than about 4.5 to about 5.5;

E) applying to one or both of the nonwoven substrate surfaces which are adjacent to said layer of threadlines and/or to the surfaces of said plurality of elongated spandex threadlines a hot melt adhesive having a temperature of from about 300° F. to about 325° F.;

F) contacting the adhesive-containing surfaces of said nonwoven substrates and/or said plurality of elongated threadlines with each other under conditions sufficient to adhesively bond said plurality of elongated spandex threadlines to both of the adjacent surfaces of said nonwoven substrates; and G) after adhesively bonding said plurality of elongated threadlines to both of the surfaces of said at least two nonwoven substrates, allowing said plurality of elongated threadlines to relax, to thereby provide said elastic multilayer composite laminate structure.

In the process at least one relatively inelastic substrate, for example a nonwoven substrate, is provided for subsequent conversion to an elasticized composite material which is suitable for use in the disposable hygiene product or article of apparel. Also provided is a film or one or more fibers or filaments of a particular type of polyurethane or polyurethaneurea material. Such polyurethane or polyurethane materials include as its soft segment base a polyglycol which includes a poly(tetramethylene-co-alkylene ether)glycol comprising constituent units which may be prepared by copolymerizing tetrahydrofuran and a $C_2$ or $C_3$ alkylene oxide. The portion of the units derived from $C_2$ or $C_3$ alkylene oxide should comprise at least 15 mole % of this poly(tetramethylene-co-alkylene ether)glycol in this polyurethane, such as from 15 mole % to 80 mole %. The $C_2$ alkylene oxide is ethylene oxide and the $C_3$ alkylene oxide may be 1,3-propylene oxide or 1,2-propylene oxide.

The polyurethane material (in the form of a film, fiber or filament) is or are elongated in at least one direction to a draft of from greater than about 4.5 to about 6, such as up to about 5.5. Next, a hot melt adhesive having a temperature of from about 280° F. to about 350° F. is applied to at least one surface of the relatively inelastic substrate and/or to at least one surface of the elongated polyurethane film or elongated fiber(s) or filament(s). The adhesive-containing surfaces of the relatively inelastic substrate and/or the elongated film or spandex fiber(s) or filament(s) are then contacted with each other under conditions sufficient to adhesively bond the elongated polyurethane film or elongated fiber(s) or filament(s) to the relatively inelastic substrate. Finally, after the relatively inelastic substrate has been adhesively bonded to the elongated polyurethane film or elongated fiber(s) or filament(s), the elongated polyurethane film or elongated fiber(s) or filament(s) is/are allowed to relax. This then provides a resulting elastic composite structure which can be used as, or converted into, a component for disposable hygiene products or articles of apparel.

DETAILED DESCRIPTION OF THE INVENTION

For the purposes of this invention, the term polyurethane is meant to include both polyurethanes (such as where a diol as used as a chain extender) and polyurethaneurea compositions (such as where a diamine or water is used as a chain extender). The polyurethane compositions may also be prepared with a mixture of one or more chain extenders such as one or more diols, one or more diamines, or combinations of one or more diols, diamines and water.

The process of the present invention involves the elasticizing of material, e.g, relatively inelastic flexible substrates, that can be used as or in stretchable components for disposable hygiene products or articles of apparel. Such substrates are elasticized by adhesively bonding thereto a certain type and form of polyurethane elastomeric material, such as films, fibers or filaments, while the polyurethane is drafted into an elongated condition. (For purpose of this invention, the terms "fibers" and "filaments" can be used interchangeably.) The elongated polyurethane material (i.e., film, fiber(s) or filament(s)) bonded to the relatively inelastic substrates is then allowed to relax, thereby providing the polyurethane-containing composite structure in its desired elasticized form.

Disposable Hygiene Products

The composites which are elasticized in accordance with the present invention can be any type of flexible structure that can be used as or converted into components which, in one embodiment, are useful for incorporation into or onto disposable hygiene products. Disposable personal hygiene products can be any product which serves to facilitate, improve, enhance or preserve the hygiene of persons or animals using the product. Non-limiting examples of disposable hygiene products include disposable diapers; training pants; adult incontinence devices and products; catamenial devices, garments and products; bandages; wound dressings; surgical drapes, surgical gowns, surgical or other hygienic protective masks, hygienic gloves, head coverings, head bands, ostomy bags, bed pads, bed sheets, and the like.

Such products may or may not be useful for also absorbing body fluids. Products of this type are further generally disposable in the sense that they are used only once or at most a few times and/or for only a relatively short period of time, and are then discarded. They are generally not washed, cleaned, refurbished or reconditioned and then reused.

Hygiene Product Components

The components which are made from the composite structures elasticized in accordance with the process herein can be used as or in elements found within disposable hygiene products of the foregoing types. Such elements can include, for example, front, back and side panels, leg cuffs, and/or waist bands of diapers or training pants. These hygiene product components can be prepared, for example, by converting the elastic composite structure material as prepared herein in bulk form into separate individual segments of size and configuration suitable for incorporation into individual disposable personal hygiene products.

Apparel Article Components

The composite structures as prepared herein can, in other embodiments, also be used as or converted into elastic components for incorporation into conventional articles of apparel. Such apparel articles can include, for instance, shirts, pants, underwear, lingerie, sweaters, jackets, coats, hats, socks, gloves, headbands, and the like. Such components can be used in or for any part of the apparel article wherein elastic or stretch properties are to be imparted. Thus such components can be incorporated, for example, into collars, cuffs, waistbands, linings, and the like.

Relatively Inelastic Substrates

The elasticized composite structures prepared in accordance with the process herein will comprise at least one relatively inelastic substrate. For purposes of this invention, the term "substrate" is used in its broadest sense to mean a flexible or deformable structure or element which has at least one surface onto which the selected elasticizing polyurethane materials used herein can be adhesively bonded. Such substrates will generally be flexible substrates with two surfaces, e.g., upper and lower, and can be in the form of films, woven or knitted substrates, mesh or scrim substrates or nonwoven substrates. Such substrates will also be relatively inelastic. Relatively inelastic substrates are those which can be elongated no more than about 120% in any direction without rupture or those which exhibit growth of more than 30% of the elongated length after elongation to 50% of the break elongation and removal of the elongating force.

Preferred relatively inelastic substrates for elasticizing herein will be in the form of nonwoven substrates. Nonwoven substrates or "webs" are substrates having a structure of individual fibers, filaments or threads that are interlaid, but not in an identifiable, repeating manner. Nonwoven substrates can be formed by a variety of conventional processes such as, for example, meltblowing processes, spunbonding processes and bonded carded web processes.

Meltblown substrates or webs are those made from meltblown fibers. Meltblown fibers are formed by extruding a molten thermoplastic material through a plurality of fine, usually circular, die capillaries as molten thermoplastic material or filaments into a high velocity gas (e.g. air) stream. This attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, U.S. Pat. No. 3,849,241, which patent is incorporated herein by reference.

Spunbonded substrates or "webs" are those made from spunbonded fibers. Spunbonded fibers are small diameter fibers formed by extruding a molten thermoplastic material as filaments from a plurality of fine, usually circular, capillaries of a spinerette. The diameters of the extruded filaments are then rapidly reduced as by, for example, eductive stretching or other well-known spun-bonding mechanisms. The production of spun-bonded nonwoven webs is illustrated, for example, in U.S. Pat. Nos. 3,692,618 and 4,340,563, both of which patents are incorporated herein by reference.

The relatively inelastic substrates to be elasticized by the process of this invention can be constructed from a wide variety of materials. Suitable materials, for example, can include: polyethylene, polypropylene, polyesters such as polyethylene terephthalate, polybutane, polymethyidentene, ethylenepropylene co-polymers, polyamides, tetrablock polymers, styrenic block copolymers, polyhexamethylene adipamide, poly-(oc-caproamide), polyhexamethylenesebacamide, polyvinyls, polystyrene, polyurethanes, polytrifluorochloroethylene, ethylene vinyl acetate polymers, polyetheresters, cotton, rayon, hemp and nylon. In addition, combinations of such material types may be employed to form the relatively inelastic substrates to be elasticized herein.

Preferred substrates to be elasticized herein include structures such as polymeric spunbonded nonwoven webs. Particularly preferred are spunbonded polyolefin nonwoven webs having a basis weight of from about 10 to about 40 grams/$m^2$. More preferably such structures are polypropylene spunbonded nonwoven webs having a basis weight of from about 14 to about 25 grams/$m^2$. A particular type of preferred composite structure in the form of a multilayer laminate using nonwovens of this type is described in greater detail hereinafter.

Elasticizing Polyurethane Material

The relatively inelastic substrates as hereinbefore described can be elasticized in accordance with the process herein by adhesively bonding to one or more of such substrates a certain type of elastomeric polyurethane material. Such adhesive bonding to the substrate to be elasticized occurs while the polyurethane material is drafted to an elongated state.

As used herein, the term "spandex" has its customary definition which is a fiber including a long chain synthetic polymer comprised of at least 85% by weight of a segmented polyurethane or polyurethaneurea. The segmented polyurethane or polyurethaneurea comprises both "soft segments" and "hard segments". The soft segments are generally polyether-based portions of the polymer chain, and, for the polyurethane materials used herein, comprise a certain type of copoly(alkylene ether)glycol. The hard segments refer to the portions of the polymer chains which are derived from the reaction of an organic diisocyanate with a diol or diamine chain extender. Spandex is also commonly referred to as elastane.

The segmented polyurethanes or polyurethaneureas used in this invention are made from a poly(tetramethylene-co-alkylene ether)glycol and, optionally, another polymeric glycol; at least one diisocyanate; and a difunctional chain extender or mixture of difunctional chain extenders. The poly(tetramethylene-co-alkylene ether)glycol or glycol mixture containing it is first reacted with at least one diisocyanate to form an NCO-terminated prepolymer (a "capped glycol"). This prepolymer is then dissolved in a suitable solvent, such as dimethylacetamide, dimethylformamide, or N-methylpyrrolidone, and then reacted with a difunctional chain extender. Polyurethanes are formed when the chain extenders are diols. Polyurethaneureas, a sub-class of polyurethanes, are formed when the chain extenders are diamines.

The poly(tetramethylene-co-alkylene ether)glycols used in making the polyurethanes, polyurethaneureas, or spandex used in the present invention can comprise constituent units derived by copolymerizing tetrahydrofuran with one or more of ethylene oxide, 1,2-propylene oxide, and 1,3-propylene oxide, wherein the percentage of ethylene and/or propylene ether moieties in the resulting glycol copolymer is greater than about 15 mole %, or even greater than about 20 mole %. The mole percent of the ethylene and/or propylene ether moieties in this copolymer glycol may range from about 15 mole % to about 80 mole % percent, including from about 15 mole % to about 70 mole %, from about 20 mole % to about 80 mole %, from about 20 mole % to about 70 mole % and from about 37 mole % to about 70 mole %. An example of a suitable polyurethane or polyurethaneurea is derived from a poly(tetramethylene-co-ethylene ether)glycol wherein the ethylene ether content in this copolymer glycol ranges from about 37 mole % to about 70 mole %.

The poly(tetramethylene-co-alkylene ether)glycols suitable for making the polyurethanes or polyurethaneureas used in the present invention can be made by the method disclosed in U.S. Pat. No. 4,139,567, incorporated herein by reference. Poly(tetramethylene-co-alkylene ether)glycols used in making the polyurethanes or polyurethaneureas for the spandex used in the present invention can have a number average molecular weight of about 650 Daltons to about 4000 Daltons, more preferably from about 1500 Daltons to about 3500 Daltons.

The poly(tetramethylene-co-alkylene ether)glycols used to make the polyurethane or polyurethaneureas can optionally include at least one additional component, such as for example 3-methyltetrahydrofuran or other diols incorporated in small amounts as molecular weight control agents. Such optional materials can also be used in making the polyurethanes and polyurethaneureas used in the present invention and are included in the meaning of the terms "poly(tetramethylene-co-alkylene ether)glycol" or "polymeric glycol". The at least one additional component may be a comonomer of the copolymeric glycol or it may be another material that is blended with the poly(tetramethylene-co-alkylene ether)glycol as part of the "polymeric glycol". The at least one additional component may be present to the extent that it does not detract from the beneficial aspects of the invention.

It has been found that elastomeric material comprising polyurethanes or polyurethaneureas made from copolymer glycols of the foregoing type can be especially useful for elasticizing substrates for eventual use as components of disposable hygiene products or articles of apparel. This is because elastomeric material of this selected composition can be drafted to desirably high elongation values and can then be adhesively bonded to relatively inelastic substrates without experiencing excessive instances of breaks at temperatures of hot melt adhesive application.

As indicated, the selected copolymer glycols hereinbefore described and optionally other polymeric glycols can be reacted with organic diisocyanates and chain extenders to provide the polyurethanes or polyurethaneureas to be used herein. Diisocyanates that can be used include, but are not limited to, 1-isocyanato-4-[(4-isocyanatophenyl)methyl]benzene, 1-isocyanato-2-[(4-cyanatophenyl)methyl]benzene, bis(4-isocyanato-cyclohexyl)methane, 5-isocyanato-1-(isocyanatomethyl)-1,3,3-trimethy-lcyclohexane, 1,3-diisocyanato-4-methyl-benzene, 2,2'-toluenediisocyanate, 2,4'-toluenediisocyanate, and mixtures thereof. The preferred diisocyanates are 1-isocyanato-4-[(4-isocyanatophenyl)methyl]benzene, 1-isocyanato-2-[(4-cyanato-phenyl)methyl]benzene, and mixtures thereof. A particularly preferred diisocyanate is 1-isocyanato-4-[(4-isocyanatophenyl)methyl]benzene.

When a polyurethane is desired, the chain extender or mixture of chain extenders used should be a diol. Examples of such diols that may be used include, but are not limited to, ethylene glycol, 1,3-propanediol, 1,2-propylene glycol, 3-methyl-1,5-pentanediol, 2,2-dimethyl-1,3-trimethylene diol, 2,2,4-trimethyl-1,5-pentanediol, 2-methyl-2-ethyl-1,3-propanediol, 1,4-bis(hydroxyethoxy)benzene, 1,4-butanediol, and mixtures thereof. The diol chain extender may have between 0 and about 10 mole percent of other chemically different additional chain extenders.

When a polyurethaneurea is desired, the chain extender or mixture of chain extenders should be a diamine. Examples of such diamines that may be used include, but are not limited to, hydrazine, ethylene diamine, 1,2-propanediamine, 1,3-propane-diamine, 1,2-butanediamine (1,2-diaminobutane), 1,3-butanediamine (1,3-diaminobutane), 1,4-butanediamine (1,4-diaminobutane), 1,3-diamino-2,2-dimethylbutane, 4,4'-methylene-bis-cyclohexylamine, 1-amino-3,3,5-trimethyl-5-aminomethylcyclohexane, 1,6-hexanediamine, 2,2-dimethyl-1,3-diaminopropane, 2,4-diamino-1-methylcyclohexane, N-methylaminobis(3-propylamine), 2-methyl-1,5-pentanediamine, 1,5-diaminopentane, 1,4-cyclohexanediamine, 1,3-diamino-4-methylcyclohexane, 1,3-cyclohexane-diamine, 1,1-methylene-bis(4,4'-diamino-hexane), 3-aminomethyl-3,5,5-trimethylcyclohexane, 1,3-pentanediamine (1,3-diaminopentane), m-xylylene diamine, and mixtures thereof. An ethylene diamine as an extender is preferred. When used, this ethylene diamine chain extender may have between 0 and 10 mole percent of other chemically different chain extenders.

Optionally, a chain terminator, for example diethylamine, cyclohexylamine, n-hexylamine, or a monofunctional alcohol chain terminator such as butanol, can be used to control the molecular weight of the polyurethane or polyurethaneurea polymer. Additionally, a higher functional alcohol "chain brancher" such as pentaerythritol, or a trifunctional "chain brancher," such as diethylenetriamine, may be used to control solution viscosity.

Polymerization of the polyurethanes and polyurethaneureas used herein can be carried out in conventional fashion using appropriate catalysts, solvents and procedures. These aspects of the preparation of polyurethanes and polyurethaneureas based on poly(tetramethylene-co-alkylene ether)glycol are described in greater detail in U.S. Pat. No. 6,639,041 and in U.S. Published Patent Application Nos. 2006/0276610; 2006/0270821; 007/0117591 and 2007/0117953. All of these patent documents are incorporated herein by reference in their entirety.

The selected types of polyurethanes and polyurethaneureas based on poly(tetramethylene-co-alkylene ether)glycols as hereinbefore described can be used to provide elastomeric material in a wide variety of forms. Solutions of these polyurethane materials can be cast into films or spun into spandex fibers or filaments. Spandex in the form of fibers or filaments is most commonly used in elasticizing substrates in accordance with the process herein for eventual conversion into components of disposable hygiene products.

Spandex fibers can be formed from the polyurethane or polyurethaneurea polymer solution through fiber spinning processes such as dry spinning, wet spinning, or melt spinning. In dry spinning, a polymer solution comprising a polymer and solvent is metered through spinneret orifices into a spin chamber to form a filament or filaments. Polyurethaneureas are typically dry-spun or wet-spun when spandex fibers made therefrom are desired. Polyurethanes are typically melt-spun when spandex fibers made therefrom are desired.

Typically, a polyurethaneurea polymer is dry spun into filaments from the same solvent as has been used for the polymerization reaction. Gas is passed through the chamber to evaporate the solvent to solidify the filament(s). Filaments are dry spun at a windup speed of at least 200 meters per minute. The spandex useful in the present invention can be spun at a speed at any desired speed such as in excess of 800 meters/minute. As used herein, the term "spinning speed" refers to the yarn take-up speed.

Good spinability of spandex filaments is characterized by infrequent filament breaks in the spinning cell and in the wind up. The spandex can be spun as single filaments or can be coalesced by conventional techniques into multi-filament yarns. Each filament in multifilament yarn can typically be of textile decitex (dtex), e.g., in the range of 6 to 25 dtex per filament.

Spandex in the form of a single filament or a multifilament yarn is typically used for elasticizing substrates to form the composite structures herein. Multifilament spandex yarn frequently will comprise from about 4 to about 120 filaments per strand of yarn. Spandex filaments or yarns which are especially suitable are those ranging from about 200 to about 3600 decitex, including from about 200 decitex to about 2400 decitex and from about 540 to about 1880 decitex.

Hot Melt Adhesive

The selected type of polyurethane elasticizing agent as hereinbefore described will be in the form of a structure or element which is adhesively bonded or attached to the relatively inelastic substrates being elasticized. Adhesive bonding of the selected type of polyurethane herein to such inelastic flexible substrates in accordance with the process herein is generally brought about through the use of a conventional hot melt adhesive.

Conventional hot melt adhesives are typically thermoplastic polymers which exhibit high initial tack, provide good bond strength between the components and have good ultraviolet and thermal stability. Preferred hot melt adhesives will be pressure sensitive. Examples of suitable hot melt adhesives are those comprising a polymer selected from the group consisting of styrene-isoprene-styrene (SIS) copolymers; styrene-butadiene-styrene (SBS) copolymers; styrene-ethylene-butylene-styrene (SEBS) copolymers; ethylene-vinyl acetate (EVA) copolymers; amorphous poly-alpha-olefin (APAO) polymers and copolymers; and ethylene-styrene interpolymers (ESI). Most preferred are adhesives based on styrene-isoprene-styrene (SIS) block copolymers. Hot melt adhesives are commercially available. They are marketed under designations such as H-2104, H-2494, H-4232 and H-20043 from Bostik; HL-1486 and HL-1470 from H.B. Fuller Company; and NS-34-3260, NS-34-3322 and NS-34-560 from National Starch Company.

Elasticizing Process

In accordance with the process of the present invention, the polyurethane film or one or more fibers or filaments of the selected type hereinbefore described will be elongated in at least one direction and while in the elongated condition will be adhesively bonded to at least one of the relatively inelastic substrates which are to be elasticized. Generally in this step of the process, the polyurethane material in whatever desired form will be stretched to a draft of from greater than about 4.5 (350% elongation) to about 5.5 (450% elongation) prior to bonding with the relatively inelastic substrate. More preferably, the polyurethane elasticizing agent will be stretched to a draft of from about 5.0 (400% elongation) to about 5.4 (440% elongation).

Drafting of the polyurethane elasticizing agent to the desired extent can be brought about by the application of stretching force to the polyurethane in the machine direction. In commercial production operations, such elongating force can be applied by means of adjustment of the speed of, and/or tensioning force applied by, the feed rolls of the polyurethane material and the wind-up rolls for the elasticized product being produced. Sets of tensioning rollers may also be employed to provide or assist in polyurethane elongation.

Also provided, generally concurrently with provision of the elongated polyurethane material, will be at least one type of relatively inelastic substrate material as hereinbefore described, to which the elongated polyurethane is to be adhesively bonded. As noted, this material will generally be a substrate in the form of a film or a woven or nonwoven substrate. Like the polyurethane, such relatively inelastic substrate material can be provided from feed rolls.

Frequently, more than one substrate can be provided for bonding with the polyurethane material. For example, film or woven or non-woven substrates can be provided to produce laminates with the elasticizing polyurethane material forming an inner layer between two outer layers of the relatively inelastic substrates. A preferred composite laminate structure of this type is described more fully hereinafter. Multilayer laminates with two or more layers of polyurethane material and three or more layers of relatively inelastic substrates may also be prepared in accordance with the process herein.

After or as the polyurethane elasticizing agent has been or is being elongated, and before, as, or even after the polyurethane material is contacted with substrate(s) of the structure being elasticized, the hot melt adhesive is applied, e.g., sprayed or coated onto one or more of the surfaces of the polyurethane material and/or the substrate(s) of the structure being elasticized. The surfaces of the elongated polyurethane and the relatively inelastic substrate(s) are then brought into and maintained in contact with each other in any suitable manner such that at least some adhesive material is interposed between at least some portions of the surfaces of the elements which are to be bonded together.

The hot melt adhesive need not be applied to the surface of the polyurethane material and/or the substrate(s) of the composite structure being elasticized in a manner which forms a continuous coating of adhesive on such surfaces. In fact, the hot melt adhesive can be applied in a variety of different ways. In one method, the melted adhesive can be deposited as a discontinuous web from a spray nozzle, a process known as melt blowing. In another method, the melted adhesive can be deposited as a solid stream from a nozzle which moves in a spiral pattern as the materials to be bonded pass by the nozzle. Such a technique is known as spiral spray. Adhesive dispensed via a spray nozzle in melt-blowing or spiral spray processes can be propelled through the nozzle by means of jets of heated air which can be externally heated to temperatures at or above the melt temperature of the adhesive. Adhesive can also be applied to any of the desired surfaces in a "dot matrix" pattern or applied directly to the spandex fiber and/or to the nonwoven fabric by direct coating or spray technology.

The temperature of the hot melt adhesive at its point of contact with the polyurethane depends on the temperature of the adhesive as dispensed, the amount of adhesive used, the adhesive application technology, and the specific details of the physical arrangement of the system used to apply the adhesive. Normally, the temperature of the adhesive as it leaves the application head is used as the benchmark to define the adhesive temperature used in the process herein since the temperature of the adhesive at the time of its actual contact with the polyurethane fibers or film is hard to measure. However, it is understood that the temperature of the adhesive when it contacts the polyurethane can range from a value essentially equal to the adhesive temperature as it leaves the application head (such as in slot coat or other strand application systems such as the Sure Wrap® system made by Nordson, Inc.) to a value which is as much as 70° F. to 150° F. lower than the adhesive temperature as it leaves the application head, such as in the case of spiral spray or melt blown application systems.

The temperature of the adhesive as it leaves the application head in the process herein will generally be within the range of from about 280° F. to about 350° F. Preferably, the hot melt adhesive used is one which should be provided at a melt temperature of from about 300° F. to about 325° F. Contact of the hot melt adhesive which is within such temperature ranges at the time of contact with the polyurethane material can frequently bring the temperature of the polyurethane to a value within the range of from about 125° F. to about 300° F. At such temperatures, the selected polyurethane materials used herein, i.e., those which are based on poly(tetramethylene-co-alkylene ether)glycols, can be drafted to the extent specified herein without exhibiting an unacceptable incidence of breaks in the polyurethane material.

After the adhesive has been applied to the appropriate surfaces, the polyurethane and the substrate(s) of the composite structure being elasticized are then maintained in contact with each other under conditions sufficient to adhesively bond the elongated polyurethane film or plurality of elongated spandex fibers or filaments to the relatively inelastic substrate(s). This is generally carried out by applying pressure to the contacted materials via the processing apparatus being used in order to form the adhesive bonding between the materials. For example, the contacted polyurethane and one or more substrates, e.g., nonwovens, can be passed through a pair of nip rollers prior to being further processed and/or before being taken up on wind up rolls.

After the polyurethane material has been adhesively bonded in its elongated state to the relatively inelastic substrate(s), the resulting elasticized composite structure is allowed to relax by removing the tension which has kept the polyurethane material elongated. This allows the resulting elastic composite structure to retract, thereby forming a gathered or puckered composite structure which is stretchable and which can be converted into elastic components for disposable hygiene products or articles of apparel.

In one particular preferred embodiment, a composite laminate structure is prepared which comprises two outer layers of nonwoven substrates of substantially equal width and an inner layer of substantially parallel, equally spaced, poly(tetramethylene-co-alkylene ether)glycol-based spandex elastomeric fibers of equal decitex which are capable of complete recovery from extensions as great as 350%. In this preferred embodiment, the layer of spandex elastomeric fibers can be composed of at least eight threadlines per inch (3.15 threadlines/cm) of width, each threadline being at least 400 decitex. Preferably the number of threadlines per inch is not greater than 16 (6.30 threadlines/cm). The threadlines can be substantially parallel to each other and parallel to the edges of the two layers of nonwoven substrates.

Both of the nonwoven substrates used in such preferred composite laminate structures can be made of synthetic polymeric fibers such as polyolefin, polyester or polyamide fibers. Both of these nonwoven substrates will frequently be thermally bonded, spunbonded or hydroentangled webs. They can have basis weight values ranging from about 10 to about 30 grams/m$^2$. The three layers of such preferred composite laminate structures are bonded together by a hot melt adhesive composition which constitutes from about 5% to about 50% by weight of the composite laminate structure.

To prepare such preferred composite laminate structures, a layer of the substantially parallel spandex threadlines is stretched not less than 100% and placed on top of one of the layers of nonwoven substrate. A hot melt adhesive is applied onto the elastomeric threadlines and the underlying nonwoven layer. The other layer of nonwoven substrate is then placed on top of the adhesive-treated combination, and the combined structure is bonded by the heat of the adhesive and pressure exerted by nip rolls while the elastomeric spandex threadlines remain in the stretched condition. Alternatively, the adhesive can be applied to the spandex threadlines or to the nonwoven inner surfaces prior to the placement of the spandex threadlines between the layers of nonwoven substrates. When the bonding is completed, the tension is substantially completely released, and the composite relaxes to form the desired elastic composite laminate structure which will then be in puckered configuration.

Preparation of the composite structures described herein employing the selected type of polyurethane elasticizing agent based on poly(tetramethylene-co-alkylene ether)glycols with a C2 or C3 alkylene glycol can be carried out using conventional apparatus and processing techniques. Such apparatus and techniques are disclosed, for example, in U.S. Pat. Nos. 4,634,482; 4,720,415; 4,482,666; 6,491,776; and 6,713,415; in U.S. Patent Publication No. 2002/0119722; and in PCT Publication No. WO 80/00676, all of which patent publications are incorporated herein by reference.

The elastic composite structures prepared in accordance with the process herein can be used as, or subsequently converted into, stretchable components for use in disposable hygiene products or articles of apparel. This conversion will typically involve cutting the composite structures into lengths and configurations suitable for the particular type of hygiene product or apparel article in which such components will be used. Such conversion procedures are conventional and can be carried out at the time and location of preparation of the composite structures herein. Alternatively, preparation of the composite structures herein, and/or conversion of such composite structures prepared elsewhere, into hygiene product or apparel article components can be carried out in connection with the production of the disposable hygiene articles or apparel articles into which the elasticized components are to be incorporated, e.g., at, near or as part of a diaper production line.

The following examples are meant to be exemplary and not limiting of the embodiments described herein.

EXAMPLES

The draft potential for each of several specific types of spandex fibers is determined by running a break series on the Invista High Speed Laminator. Such testing determines the time from lamination start up until spandex fiber breakage occurs using different spandex formulations under varying conditions of spandex draft and hot melt adhesive temperature.

The High Speed Laminator is a device which produces nonwoven—spandex—nonwoven laminates using a process that simulates the process commonly used on high speed diaper production lines. This type of nonwoven—spandex fiber—nonwoven laminate is commonly made as part of the construction of a disposable diaper. In the process carried out with the High Speed Laminator, spandex fibers are elongated to a specific draft (elongation) or tension and guided in parallel, evenly spaced apart configuration to a position immediately above a sheet of a low basis weight nonwoven (commonly called the back sheet). A hot melt adhesive is applied by standard spiral spray application technology hereinafter described. The spandex fibers are then brought into direct contact with the nonwoven sheet, and a second nonwoven sheet (commonly known as the top sheet) is brought into direct contact with bottom sheet/spandex fibers assembly. The components are thus layered in the order top sheet—spandex fibers—bottom sheet, and the entire assembly is passed through a nip roll.

In this example, the adhesive application technology used in the laminator is a single spray nozzle made by Nordson, Inc. of Dawsonville, Ga. In the setup using this type of apparatus, the tip of the spray nozzle can be mounted 0.5 to 1.5 inches above the spandex fibers, and the spandex fibers at point of adhesive application can be between 0.25 and 0.5 inch above the back sheet. The linear distance between the point of adhesive application and the nip roll is generally about 8 inches, and the linear speed of the machine can commonly be run between 200 and 1000 feet per minute.

The various nonwoven, adhesive and spandex materials used, along with the specific test conditions employed in this example, are as follows:
Nonwoven: 15 grams/m$^2$ spunbond polypropylene made by Avgol, Inc.
Adhesive: H-4232 or H-20043 elastic attachment hot melt adhesive made by Bostick, Inc.
Spandex Materials Tested:
1. 540 decitex Type 262 Lycra® XA® made by Invista, Wilmington, Del. Soft segment based on 100% $C_4$ polyether glycol (polytetrahydrofuran) 2. 540 decitex D-19 spandex fiber produced by Invista, Wilmington, Del. Soft segment based on copolyether glycol composed of 38% $C_2$ and 62% $C_4$ segments, made by copolymerization of ethylene oxide and tetrahydrofuran.
Test conditions:
Five strands (filaments) of spandex used, spaced 5 mm apart.
Adhesive add on: 8.0 mg/in$^2$.
Laminator speed: 300 ft/min.
Distance from adhesive spray nozzle tip to spandex strands: 1.0 in.
Distance from spandex strands to nonwoven back sheet: 0.2 inch.
Distance from adhesive application point to nip roll: 8 inches
Test Procedure:
The laminator machine is started. When test conditions are reached, the time in minutes until fiber breakage occurs is recorded, with recording continuing until all five spandex strands break. Reported break times are an average of the times it takes for each of the five spandex strands to break. If the laminator runs for more than five minutes with no spandex strands breaking, this is taken as an indication that the lamination process can be successfully carried out at those conditions without excessive strand breakage, and the test under those conditions is then discontinued. Comparison examples (Comp. 1-8) include a spandex prepared with poly(tetramethylene)glycol, while the inventive examples (INV. 1-8) include a spandex prepared with a poly(tetramethylene-co-ethylene ether)glycol.

Break time results are shown in Tables I and II.

TABLE I

Test No. 1
Adhesive temperature 300° F., spiral air temperature 330° F.

| Spandex | Draft | Time to break (minutes) |
|---|---|---|
| Comp. 1 | 4.5 | Greater Than 5 min. |
| Comp. 2 | 5.0 | 0.4 |
| Comp. 3 | 5.5 | 0.2 |
| Comp. 4 | 6.0 | 0.2 |
| INV. 1 | 4.5 | Greater Than 5 min. |
| INV. 2 | 5.0 | Greater Than 5 min. |
| INV. 3 | 5.5 | Greater Than 5 min. |
| INV. 4 | 6.0 | 1.7 |

TABLE II

Test No. 2
Adhesive temperature 325° F., spiral air temperature 355° F.

| Spandex | Draft | Time to break (minutes) |
|---|---|---|
| Comp. 5 | 4.5 | Greater Than 5 min. |
| Comp. 6 | 5.0 | 0.3 |
| Comp. 7 | 5.5 | 0.4 |
| Comp. 8 | 6.0 | 0.1 |
| INV. 5 | 4.5 | Greater Than 5 min |
| INV. 6 | 5.0 | Greater Than 5 min |
| INV. 7 | 5.5 | Greater Than 5 min. |
| INV. 8 | 6.0 | 1.5 |

The Table I and Table II data indicate that the selected high draft potential spandex materials which are used in the present process for making elastic composites and which comprise soft segments based on poly(tetramethylene-co-ethylene ether)glycol exhibit improved breakage performance when used at higher draft values and higher hot melt adhesive temperatures in comparison with a spandex material which is otherwise comparable but which has soft segments based on poly(tetramethylene ether) glycol.

While the present invention has been described in an illustrative manner, it should be understood that the terminology used is intended to be in a nature of words or description rather than of limitation. Furthermore, while the present invention has been described in terms of several illustrative embodiments, it is to be appreciated that those skilled in the art will readily apply these teachings to other possible variations of the invention.

What is claimed is:

1. An article comprising at least one relatively inelastic substrate, a polyurethane material selected form the group consisting of a film and one or more filaments comprising as the soft segment base of said polyurethane material is a polyglycol comprising a poly(tetramethylene-co-alkylene ether) glycol comprising constituent units derived by copolymerizing tetrahydrofuran and a $C_2$ or $C_3$ alkylene oxide, wherein the portion of the units derived from $C_2$ or $C_3$ alkylene oxide comprises at least 15 mole % of said poly(tetramethylene-coalkylene ether)glycol; and a hot melt adhesive having a temperature of from about 260° F. to about 350° F.

2. The article of claim 1, wherein said polyurethane material is elongated to a draft greater than about 4.5.

3. The article of claim 1, wherein said alkylene oxide is ethylene oxide.

4. The article of claim 1, wherein said article is included in or converted to an apparel article or a disposable hygiene product.

5. The article of claim 4, where in said apparel article or disposable hygiene product is selected from the group consisting of disposable diapers; training pants; adult incontinence devices and products; catamenial devices, garments and products; bandages; wound dressings; surgical drapes, surgical gowns, hygienic protective masks, hygienic gloves, head coverings, head bands, ostomy bags, bed pads, and bed sheets.

6. A process for making an elastic composite structure, which process comprises:
A) providing at least one relatively inelastic substrate;
B) providing a polyurethane material selected form the group consisting of a film and one or more filaments comprising as the soft segment base of said polyurethane material a polyglycol comprising a poly(tetramethylene-co-alkylene ether)glycol comprising constituent units derived by copolymerizing tetrahydrofuran and a $C_2$ or $C_3$ alkylene oxide, wherein the portion of the units derived from $C_2$ or $C_3$ alkylene oxide comprises at least 15 mole % of said poly(tetramethylene-co-alkylene ether)glycol;
C) elongating in at least one direction said polyurethane material to a draft of from greater than about 4.5 to about 5.5;
D) applying to at least one surface of said at least one relatively inelastic substrate and/or to at least one surface of said elongated polyurethane material a hot melt adhesive having a temperature of from about 260° F. to about 350° F.;
E) contacting the adhesive-containing surfaces of said at least one relatively inelastic substrate and/or said polyurethane material with each other under conditions sufficient to adhesively bond said elongated polyurethane material to said at least one relatively inelastic substrate; and
F) after adhesively bonding said elongated polyurethane material to said at least one relatively inelastic substrate, allowing said polyurethane material to relax, to thereby provide said elastic composite structure.

7. The process of claim 6, wherein said alkylene oxide is ethylene oxide.

8. The process of claim 6, wherein said relatively inelastic substrate is suitable for use in a disposable hygiene product or an article of apparel.

9. The process according to claim 6, wherein said polyurethane has a number average molecular weight of from about 650 to about 4000 Daltons and is in the form of a plurality of filaments.

10. The process according to claim 9, wherein each of the filaments in the plurality of spandex filaments ranges from about 200 to about 3600 decitex.

11. The process according to claim 10, wherein the polyglycol of the soft segment base of said spandex material comprises poly(tetramethylene-co-ethylene ether)glycol comprising constituent units derived by copolymerizing tetrahydrofuran and ethylene oxide wherein the portion of the units derived from ethylene oxide comprises from about 37 mole % to about 70 mole % of said poly(tetramethylene-co-ethylene ether)glycol.

12. The process according claim 6, wherein said relatively inelastic substrate is a nonwoven substrate selected from at least one of polyolefin, polyester and polyimide webs.

13. The process according to claim 6, wherein said polyurethane material is elongated to a draft of from about 5.0 to about 5.4.

14. The process according to claim 6, wherein said hot melt adhesive is a pressure sensitive adhesive comprising a polymer selected from the group consisting of styrene-isoprene-styrene (SIS) copolymers; styrene-butadiene-styrene (SBS) copolymers; styrene-ethylene-butylene-styrene (SEBS) copolymers; ethylene-vinyl acetate (EVA) copolymers; amorphous poly-alpha-olefin (APAO) polymers and copolymers; and ethylene-styrene interpolymers (ESI).

15. The process according to claim 6, wherein contact of said adhesive-containing surfaces of said relatively inelastic substrate(s) and/or said polyurethane material with each other brings the temperature of said spandex material to within the range of from about 125° F. to about 300° F.

* * * * *